United States Patent [19]

Bartelt

[11] 4,295,468

[45] Oct. 20, 1981

[54] CARDIAC PACER TESTING SYSTEM

[75] Inventor: James T. Bartelt, Shoreview, Minn.

[73] Assignee: Cardiac Pacemakers, Inc., St. Paul, Minn.

[21] Appl. No.: 87,867

[22] Filed: Oct. 24, 1979

[51] Int. Cl.³ .............................................. A61N 1/36
[52] U.S. Cl. ............................................ 128/419 PT
[58] Field of Search ................... 128/419 PG, 419 PT

[56] References Cited

U.S. PATENT DOCUMENTS

| | | | |
|---|---|---|---|
| 3,669,120 | 6/1972 | Nielsen | 128/419 PG |
| 3,800,801 | 4/1974 | Gaillard | 128/419 PT |
| 3,830,242 | 8/1974 | Greatbatch | 128/419 PT |
| 3,865,119 | 2/1975 | Svensson et al. | 128/419 PT |
| 4,142,533 | 3/1979 | Brownlee et al. | 128/419 PT |

*Primary Examiner*—William E. Kamm
*Attorney, Agent, or Firm*—Orrin M. Haugen; Thomas J. Nikolai

[57] ABSTRACT

A hand-held, portable, battery-powered test instrument for evaluating the performance of cardiac pacer devices prior to the implantation thereof and afterwards. To test R-wave sensitivity of a pacer device, a series of simulated R-waves, each of a predetermined greater amplitude, is applied to the pacer unit under test, each such simulated R-wave occurring at a time following a preceding pacer pulse sufficient to ensure that the pacer's refractory period has elapsed. This process is continued until a succeeding pacer pulse does not occur at the time it would otherwise be due, thus indicating that the R-wave had just reached the amplitude sufficient to cause the resetting of the pacer pulse generator. A count is maintained of the number of cycles needed to cause resetting of the pacer pulse generator and this value is displayed to indicate, in terms of voltage, the minimum amplitude of the R-wave just sufficient to result in pacer resetting.

6 Claims, 8 Drawing Figures

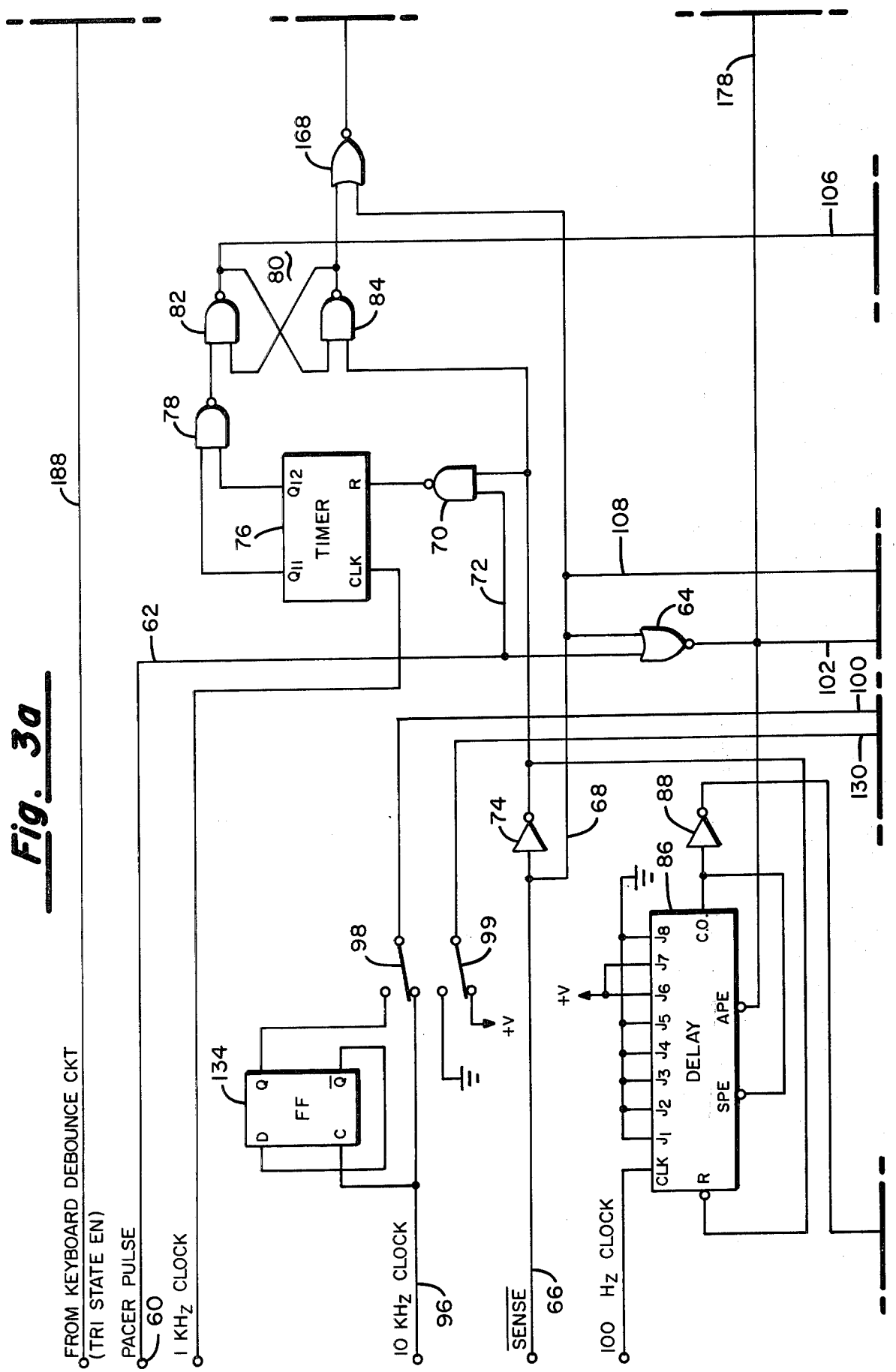

CARDIAC PACER TESTING SYSTEM

BACKGROUND OF THE INVENTION

I. Field of the Invention:

This invention relates generally to electronic test apparatus, and more specifically to a device for determining the amplitude threshold at which an electronic device will respond to an input stimulus.

II. Discussion of the Prior Art:

The present invention will be described in association with cardiac pacer apparatus in that it has been particularly developed for use in testing and evaluating heart pacers. It is to be understood at the outset, however, that the present invention may be used in conjunction with other electronic apparatus where threshold sensitivity is the parameter to be measured or monitored.

As is well known in the art, a demand-type cardiac pacer can commonly be used in the treatment of cardiac irregularities on a noncompeting basis. As such, demand-type cardiac pacers include a pulse generator for producing output stimulating pulses at a predetermined rate in the absence of normal cardiac (R-wave) activity. The stimulating impulses are generally applied to the heart muscle by way of heart contacting electrodes. The same electrodes used to apply the stimulating impulses are also arranged to pick up the R-wave impulses generated during the depolarization of the heart muscle and the resulting signal is processed and employed to reset the pulse generator's timer mechanism such that the next pacer pulse will not appear on schedule, but instead, only after a predetermined time has elapsed since the detection of a preceding R-wave.

Not every impulse picked up by the heart contacting electrodes is a R-wave. Accordingly, cardiac pacer devices normally include circuitry for discriminating between R-waves and other electrical activity picked up by the electrodes. This discriminating circuitry may include band-pass filter circuits having a center frequency tuned to the normal frequency of a R-wave and, in addition, it may include a thresholding device requiring the detected signal to exceed a predetermined amplitude before it will be recognized as a true R-wave. Because of the inclusion of such threshold circuits, the attending physician has a need to measure the sensitivity or level at which a received R-wave will be capable of resetting the pacer pulse generator to thereby inhibit the generation of a pacer pulse. The present invention provides an apparatus for testing or measuring the sensitivity parameter of a pacemaker and for providing a visual display of the voltage amplitude of a waveform which is found to be just sufficient to pass the threshold criteria.

Various threshold analyzing devices are known in the art. For example, reference is made to the Herrmann U.S. Pat. No. 3,757,790, the Thaler Pat. No. 3,837,348, the Gombrich et al U.S. Pat. No. 3,920,005. While each of the foregoing patents relates in some way to apparatus for measuring the performance characteristics of cardiac pacer devices, none describes a system whereby the sensitivity characteristic of a pacer under test can be measured and displayed.

SUMMARY OF THE INVENTION

The present invention comprises a feature embodied in a hand-held, portable, battery-powered test device for use in evaluating the operating parameters of a cardiac pacer prior to and following implantation of the pacer in a patient. While the test device in which the present invention finds application also includes the ability to measure and test a number of other parameters, as far as the present invention is concerned, the device is adapted to receive the pacer output pulses from the pacer unit under test and to apply pseudo R-waves to the R-wave sensing circuitry of the pacer under test. Upon receipt of each pacer pulse, a timer circuit is reset to initiate a new time interval of a predetermined length. In addition, the pulse generator output pulse initiates the running of a delay period and increments a device which ultimately establishes the amplitude of the pseudo R-wave to be generated by the test device. The termination of the delay period triggers a digital scanner device which then operates to successively generate a plurality of addresses which, in turn, are used to access individual storage registers of a Read Only Memory. Stored at each address in the ROM is a binary number indicative of a multiplier for a reference voltage at a given instant in time. As such, the reading out of the plurality of ROM storage registers results in the piece-by-piece construction of a predetermined signal of a desired shape and whose amplitude may be adjusted in predetermined, known increments upon the receipt of each generated pacer pulse. It is this waveform that is applied to the pacer under test and which is ultimately processed by its sensing circuitry. If the aforementioned timer circuit times out, it is known that the pacer under test has failed to produce stimulating pulse outputs and, accordingly, the pseudo R-wave applied has reached an amplitude sufficient to cause resetting of its pulse generator. At this point, a display counter which is incremented by each pulse generator pulse output is enabled and a digital readout is provided of the voltage amplitude at which pacer pulse generator resetting occurred.

OBJECTS

It is accordingly a principle object of the present invention to provide a new and improved method and apparatus for measuring the sensitivity threshold of an amplitude responsive electronic device.

Another more specific object of the invention is to provide a test apparatus for measuring the threshold at which a R-wave signal will effect resetting of a pulse generator in a demand-type cardiac pacer system.

A still further object of the invention is to provide in a portable test instrument an arrangement whereby the sensitivity threshold for a demand-type pacer can be rapidly and accurately displayed.

These and other objects and advantages of the invention will become apparent to those skilled in the art from the following detailed description of a preferred embodiment when considered in conjunction with the accompanying drawings.

DESCRIPTION OF THE PREFERRED EMBODIMENT

Figure 1:
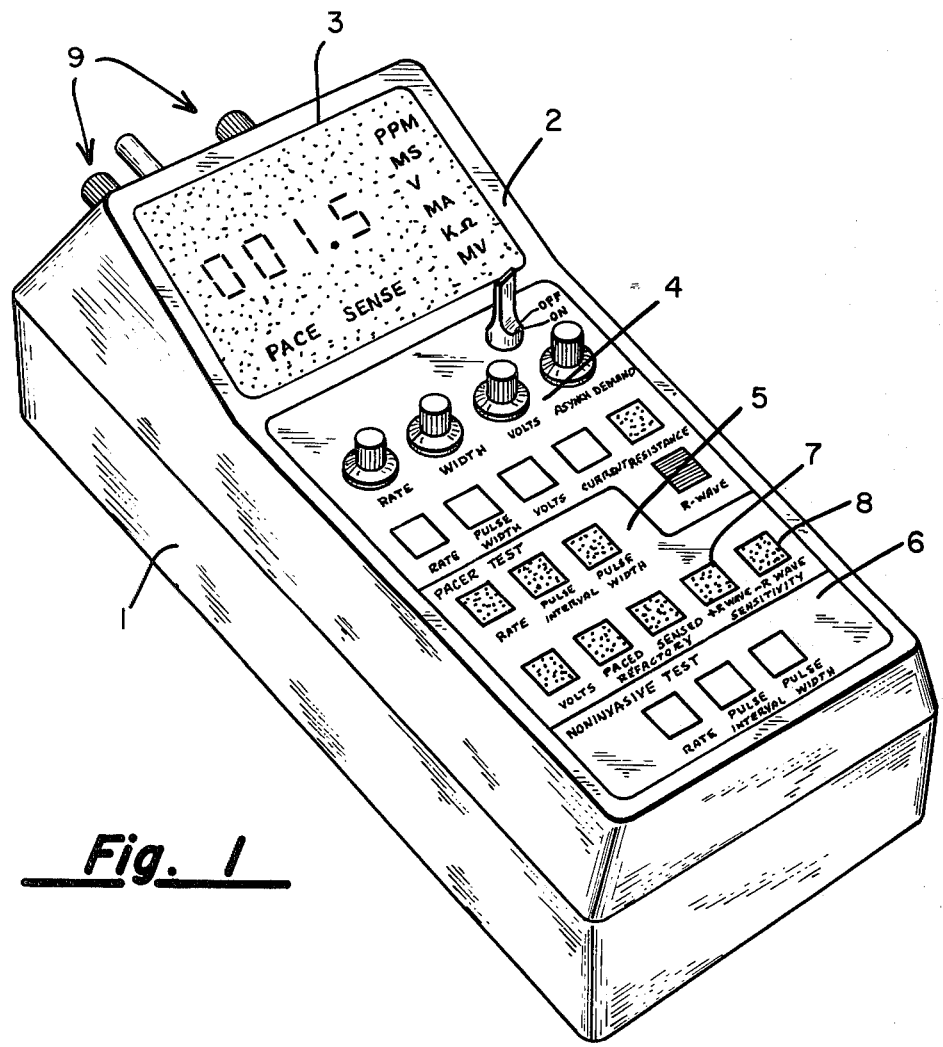
FIG. 1 shows the external feature of the test instrument in which the present invention finds usage.

Referring first to FIG. 1, the overall mechanical design features of the test instrument in which the present invention finds use will be explained. As is illustrated, the device comprises a molded plastic case 1 having a battery compartment therein for holding one or more batteries needed to power the test instrument. The housing 1 also contains a number of printed circuit boards on which are mounted various integrated circuit and discrete component devices. The front panel 2 is partitioned into four discrete areas, namely, a display area 3, a threshold test control group 4, a pacer test control group 5 and a noninvasive test control group 6. Included in each group are a plurality of push buttons and control knobs used to operate the device in its various modes. In connection with the instant application, the features of FIG. 1 which are of interest in determining R-wave sensitivity are the push buttons 7 and 8 and the display 3. Located at the top of the housing 1 are a plurality of terminals or jacks indicated generally by numeral 9. These jacks permit the internal circuitry to be connected to patient pacing leads, to a cable connectable to an external pacer to be tested or to bracelet-type electrodes worn by the patient during noninvasive test procedures. Thus, pacer pulses from a pacemaker under test may be coupled into the apparatus of FIG. 1 by a suitable cable and when either the +R-wave or the −R-wave push buttons 7 and 8 are depressed, the device will function to present on the display screen 3 a digital readout of the sensitivity of the device undertest in millivolts. This figure will appear just above the legend "sense" on the display screen 3. At the same time, a light emitting diode (LED) will be illuminated next to the legend MV on the display screen to indicate that the number being presented is in the units of millivolts.

As has been indicated, the device depicted in FIG. 1 is arranged to determine the sensitivity of a demand-type cardiac pulse generator. The term "sensitivity" refers to the amplitude that an intracardiac R-wave must have to inhibit a demand-type pulse generator. A demand pulse generator is one that measures intracardiac electrical activity to determine if the heart can beat without an external stimulus. Certain levels of heart activity have been found to indicate that the heart is beating without stimulus. If this level of activity is present, the demand pulse generator will sense this fact and inhibit the pulse generator for a predetermined interval. If during that interval no intracardiac electrical activity of sufficient magnitude and proper frequency content is sensed, the pulse generator issues a pacer pulse to stimulate the heart. The interval of the pulse generator is generally set by the manufacturer or may be chosen by the doctor to ensure that the proper heart beat will be maintained.

Figure 2:
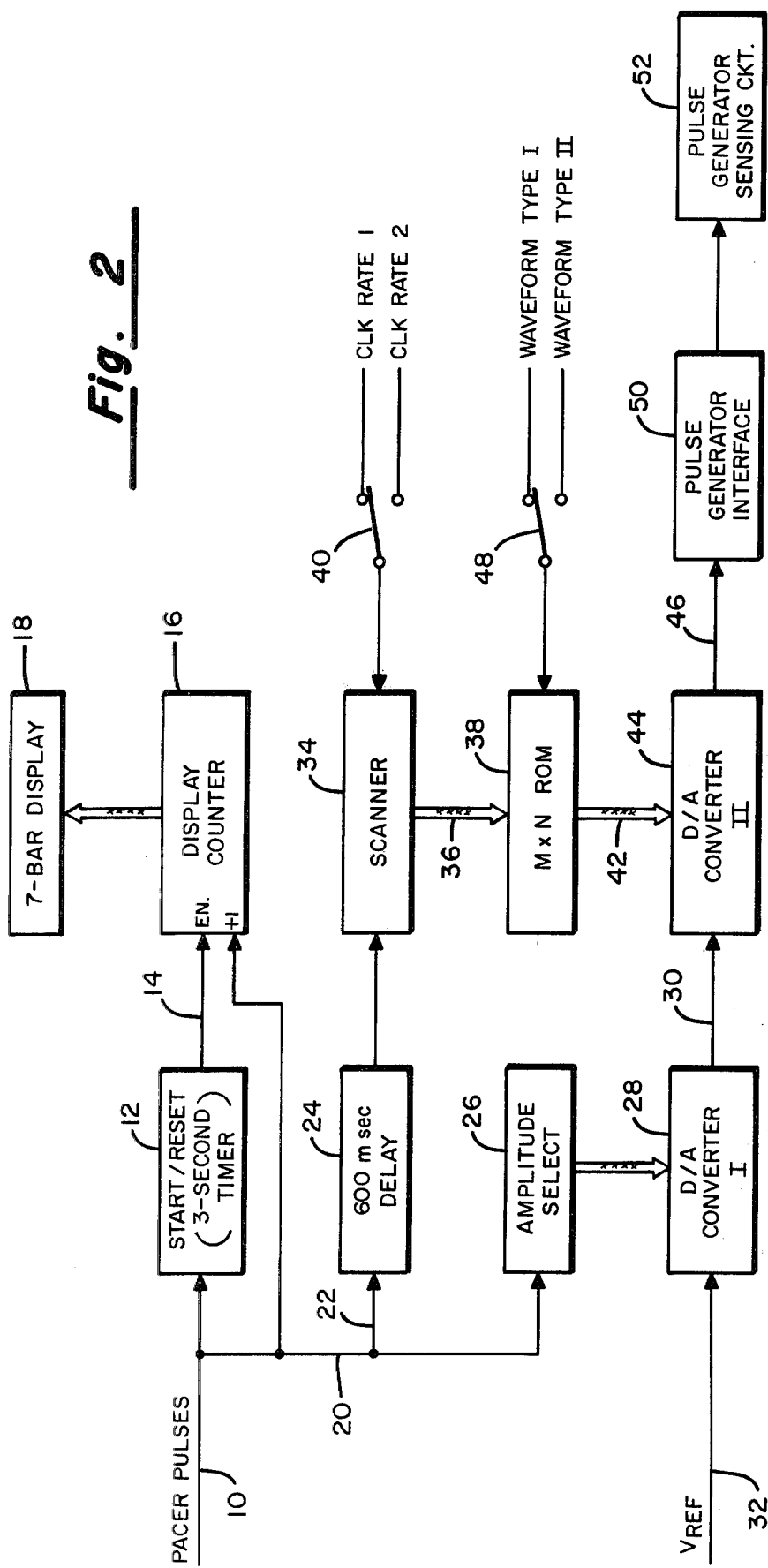
FIG. 2 is a block diagram representation of the preferred embodiment.

Referring next to the block diagram of FIG. 2, pacer pulses from a demand-type pacer (not shown) are applied to the test instrument by way of a conductor 10. Included within the test instrument is a timer 12 which is arranged to produce an output signal on its output conductor 14 whenever a predetermined time interval elapses prior to the receipt of a second input at its start/reset terminal. The length of the interval in question is set to be greater than the normal pulse-to-pulse interval of the pacemaker under test. Specifically, a time interval of three seconds has proven to be adequate.

The output from the timer device 12 is connected as an enable signal on a display counter 16 whose outputs are coupled through suitable buffer circuits (not shown in FIG. 2) to a conventional digital display device, e.g., a seven bar LED display 18. The value displayed is the number of pacer pulses produced by the pacer pulse generator before the pseudo R-wave reaches an amplitude sufficient to initiate the resetting of the pacer pulse generator's timing circuit. As will become apparent as the description proceeds, this count is also a measure of the amplitude of the pseudo R-wave signal measured in millivolts.

The pacer pulses applied to the line 10 are also conveyed by way of a line 20 to an input 22 of a delay circuit 24. The time interval of the delay is chosen to be sufficiently long so as to exceed the maximum refractory period encountered in the demand-type cardiac pacers being tested. The interval is less, however, then the normal pulse-to-pulse interval of the output from the pacer under test. It has been found that a delay value of 600 milliseconds is entirely workable. The output from the pacer pulse generator appearing on line 20 is also applied to an amplitude select circuit 26 which functions to apply a multiplier value to the digital inputs of a digital-to-analog converter 28. The output from the D/A converter 28 appearing on conductor 30 is a voltage signal proportional to the input reference potential on line 32 multiplied by a digital value as contained in the amplitude select circuit 26.

When the period of the delay circuit 24 expires, a signal is presented to a scanner circuit 34 which causes it to generate on its parallel output lines 36 a digital pattern of one's and zero's corresponding to a series of sequential addresses. These addresses are applied to a MxN Read Only Memory 38 and the rate at which the sequential addresses are applied is determined by the setting of a rate switch 40 which connects the scanner to either a first or a second source of clock signals of differing repetition rates.

Stored at sequential locations within the M×N ROM 38 are digital values corresponding to the amplitude of a pseudo R-wave at any one of up to M different time intervals. Thus, by sequentially reading out these digital values, it is possible to define the contour or shape of the pseudo R-wave. These sequential values are applied by way of the conductors in cable 42 to a second digital-to-analog converter 44. Thus, the D/A converter 44 acts as a multiplier of the voltage appearing on conductor 30 from the output of the D/A converter 28. The net result is the development on the conductor 46 of a waveform whose amplitude is dependent upon the number of pacer pulses received from an initial starting point and whose contour or shape is defined by the values stored in the ROM device 38.

To make the test device more universally acceptable as far as use with pacemaker devices manufactured and sold by different companies, it is possible to store in the ROM 38 signals defining a plurality of waveform contours which may then be selected by the setting of a switch device such as switch 48 or, alternatively, by the bit permutations of the address signals coming from the scanner 34.

To illustrate the foregoing point, Cardiac Pacemakers, Inc., the assignee of the present invention, uses as its test standard for measuring sensitivity, a pseudo R-wave which takes the shape corresponding to a half sine wave of a 22 Hz frequency. Sensitivity specifications for pulse generator models of manufacturers using square, trapezoidal, haversine or other waveforms to determine sensitivity may be encountered. As such, by providing a ROM 38 of a sufficient size, it is possible to store therein digital values which may be sequentially read out so as to re-create any of the foregoing pseudo R-waves. Switch 48 suggests the ability to uniquely select one or the other of two waveform types, it being understood that the invention is not limited to the selection of only two such waveform types.

The resulting waveform appearing on conductor 46 may be applied through a pulse generator interface circuit 50 to the pulse generator leads leading to its sensing circuit, which circuit is represented in the block diagram of FIG. 2 by the block labeled 52.

The circuit of the present invention is designed to produce pseudo R-waves of known amplitude and waveform to inhibit a demand-type pulse generator. The test circuit then displays the amplitude which is just sufficient to cause inhibition of the pulse generator. The way that this is accomplished will now be explained.

The pacer pulse generator under test produces output pulses at a given repetition rate unless inhibited by simulated R-waves. These pacer pulses are applied to line 10 and cause four separate things to happen. First, the pacer pulses reset the three second timer 12 thus initiating a new three second interval. Secondly, they initiate a 600 millisecond delay by way of the circuit 24. Each received pacer pulse on line 10 also increases the previous amplitude of the pseudo R-wave by a predetermined amount, e.g., 0.1 mv and, at the same time, causes the display counter 16 to be advanced by one. The amplitude select circuit 26 typically provides 8 bits of information to D/A Converter 28 which constitutes a multiplier factor for a stable reference voltage applied to the converter 28 by way of input line 32. This action causes the voltage appearing on line 30 to be of an amplitude proportional to the value established by the amplitude select circuit 26. This value remains constant until the receipt of the next pacer pulse on line 10.

Prior to the receipt of the next pacer pulse, however, the 600 millisecond delay established by circuit 24 expires and at that time the scanner device 34 is initiated to sequentially read out binary coded address representing signals on the address lines in the cable 36. These addresses sequentially appear at a rate determined by the setting of the switch 40. As each address is presented to the ROM 38 a N-bit information word is applied by way of cable 42 to the second D/A converter 44. The converter 44 also acts as a multiplier and thereby scales the analog voltage appearing on the conductor 30. The result is that there is produced on the output conductor 46 of a pseudo R-wave signal of a given contour (as determined by the information stored in ROM 38) and of an amplitude which increases a prescribed amount for each successive pacer pulse applied to the conductor 10.

At the instant that the 600 millisecond delay of circuit 24 expired to initiate the scanner 34, it also re-initiated a new 600 millisecond delay period. If this second 600 millisecond delay expires before a new pacer pulse appears on conductor 10, a second pseudo R-wave will be generated at the output of the interface circuit 50. When a new pacer pulse is detected before the circuit 12 times out, i.e., within the three second interval, the entire procedure previously explained is repeated. That is, the amplitude of the R-wave applied to the pulse generator sensing circuit is increased by a given known amount. However, if the timer 12 reaches the three second point without having been reset earlier by a new pacer pulse, it is an indication that the demand-type pacer has had its pulse generator inhibited. When this happens, the signal on line 14 from the timer 12 enables the display counter 16 and a digital number will be displayed at 18 indicative of the R-wave sensitivity of the pacer under test expressed in millivolts.

It has been found that the time required to make the sensitivity measurement is typically less than 15 secnds. It provides the user with the ability to verify that the sensitivity of a demand pulse generator is within desired tolerances prior to its being implanted.

Now that the overall organization and mode of operation of the device has been explained with the aid of a block diagram, consideration will be given to the specifics of an implementation deemed to constitute the best mode known for carrying out the invention.

Figure 3:
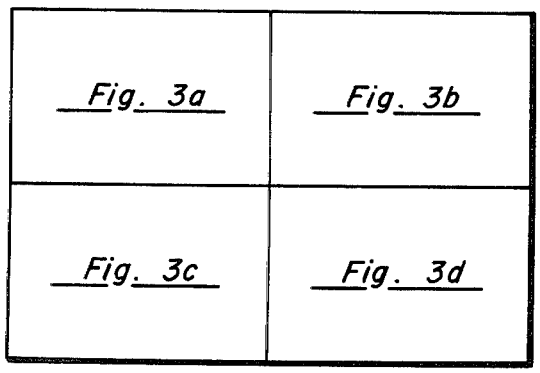
FIGS. 3a through 3d, when arranged as shown in FIG. 3, illustrate a logic diagram showing the manner in which the system depicted functionally in FIG. 2 may be realized with commercially available circuitry.

FIGS. 3a through 3d, when arranged as shown in FIG. 3, illustrate by means of a detailed logic diagram the manner in which the sensitivty testing circuitry may be implemented. Those skilled in the art will recognize that various alternatives may be employed to achieve the type of operation set out and, accordingly, the arrangement depicted in FIGS. 3a through 3d is to be considered as merely illustrative of the best mode contemplated for practicing the invention.

Pacer pulses from the pacemaker under test are coupled by accessory leads (not shown) to the terminal 60 and are applied by way of a conductor 62 to a first input of a NOR gate 64. A second input to this gate comes by way of conductors 66 and 68 from a conventional debounce circuit (not shown) associated with the push buttons 7 and 8 in FIG. 1.

The pacer pulses on line 62 are also applied as a first input to NAND gate 70 by way of conductor 72 and the second input to NAND gate 70 comes from the output of an inverter 74 whose input also receives the signals present on conductors 66. The output NAND gate 70 is applied to the reset terminal, R, of a digital timer 76 which is arranged to be advanced at a predetermined rate by 1 KHz clock pulses. As is illustrated, stages 11 and 12 of this counter have their outputs connected as inputs to a NAND gate 78. As such, when the count contained in the counter 76 reaches $3072_{10}$, which occurs approximately three seconds after the counter is reset when a 1 KHz clock source is employed, the gate 78 will toggle the flip-flop 80 comprised of the cross-coupled NAND gates 82 and 84.

The output from NOR gate 64 is also coupled to the asynchronous preload enable terminal (APE) of a binary coded decimal counter 86. As can be seen from FIG. 3a, the jam inputs $J_1$ through $J_8$ are wired to logic levels such that the binary coded decimal number 00000110 ($60_{10}$) will be preloaded into the counter each time either the APE terminal or the synchronous preload enable (SPE) terminal is stimulated. The counter 86 receives regularly occurring timing signals in the form of 100 Hz clock pulses and upon the receipt of each such clock pulse the count contained in the device 86 is decremented. As such, it will require 600 milliseconds for the count to reach zero, assuming that the device is not again reloaded prior to the expiration of that interval. The output from the binary coded decimal downcounter 86 apears at its carry overflow terminal C.O. upon the contents thereof reaching zero and this signal is coupled through an inverter stage 88 to a first input of a NAND gate 90. It can be seen then, that when the counter 86 is timed out, i.e., 600 milliseconds have expired since the receipt of a pacer pulse, a signal will be produced at the output of NAND gate 90 to stimulate the load terminals (LD) of the IC chips 92 and 94, each of which is an asynchronous programmable counter. The two are cascaded to form the scanner device 34 of FIG. 2. Specifically, the input terminals $P_1$ through $P_4$ are each tied to a logic zero level and each time the load terminal LD thereof is stimulated, the device will be preloaded with all zero's. It then begins to be incremented at a 10 KHz rate by way of clock pulses applied at the clock input terminal 96 and aplied through the selector switch 98 and a conductor 100 to the clock terminal CLK of the chips 92 and 94.

The output from the NOR gate 64 is also applied to the input terminal of a dual binary up-counter 104. It is the counter 104 that implements the amplitude select function 26 in the block diagram of FIG. 2. As is known to those skilled in the art, a dual up-counter consists of two identical, internally synchronous N-stage counters. Counter stages are D-type flip-flops having interchangeable CLK and enable (E) lines for allowing incrementation on either the positive-going or negative-going transition of the input signal thereto. The A-bank stages of the counter 104 receive a clock input at the terminal $C_A$ by way of the output from the flip-flop 80 applied thereto via conductor 106. The amplitude select circuit 104 is adapted to be reset by signals applied via conductors 66, 68 and 108.

Summarizing for a moment, then, it can be seen that pacer pulses from the unit under test are applied to the input terminal 60 and from there are applied through various logic devices to initiate the running of the timer circuit 76, the delay circuit 86 and the amplitude select circuit 104. Each such pacer pulse serves to increment the counter 104. The counter is reset when the push button switch 7 or 8 of FIG. 1 is released, this signal being applied to the reset terminals R by way of the conductors 66, 68 and 108.

The outputs from the amplitude select circuit 104 are, in turn, coupled as inputs to a multiplying digital-to-analog converter 110. Applied to the reference voltage input $V_{REF}$ (+) is a predetermined reference voltage whose magnitude is determined by the voltage applied to conductor 112 when the drops across the resistor 114 and the potentiometer 116 are considered. The multiplying D/A converter causes a current to flow through the output conductor 118 which is proportional to the fixed reference voltage and the binary contents of the amplitude select circuit 104. This current is converted to a voltage signal by means of an operational amplifier arrangement 120 and its associated feedback resistance 122. The output from the operational amplifier 120, then, serves as the $V_{REF}$ (+) signal for a second multiplying D/A converter 124.

Associated with the D/A converter 124 is a M×N ROM 126. Specifically, the output from the ROM is applied to the individual input stages of the D/A converter 124. Address representing signals are arranged to be applied to the ROM by way of the conductors 128 which, in turn, are connected to the output terminals of the scanner device comprised of the programmable counters 92 and 94. Accordingly, it is the output from the scanner which is made to access a data word stored in the ROM 126 and it is this data word that comprises the multiplying factor for the analog voltage present on the $V_{REF}$ (+) terminal of the D/A converter 124.

When a Preload Enable (PE) and a load LD signal are simultaneously applied to the scanner chips 92 and 94 the initial address applied to stages 0 through 7 of the ROM 126 will be all zero's. Stage 8 of the ROM is shown as being connected by a conductor 130 to a pole of the double pole-double throw switch 99. As such, either a binary zero or a binary one signal may selectively be applied to the highest order stage of the ROM. In this manner, the function performed by the switch 48 in FIG. 2 is realized. That is, the M×N ROM may effectively be partitioned into two halves and considering the device 126 to be a 512×8 bit device, signals characteristic of a first waveform may be stored in the lower 256 addresses while signals characteristic of a different waveform may be stored in the upper 256 bits. The state of the signal on conductor 130 determines whether the lower half or upper half will be accessed.

The rate at which the addresses of the ROM will be sequentially presented thereto is determined by the clock rate of the signals applied to the clock input terminals of the scanner chips 92 and 94. As can be seen from the logic drawing, when the switch 98 is in a first position, the clock rate for the scanner will be 10 KHz which is significantly higher than the normal time period one would expect between the conclusion of the timing out of the delay circuit 86 and the point at which a subsequent pacer pulse would be expected. As such, the combination of the ROM outputs and the D/A converter 124 can create a current waveform on conductor 132 which is representative of the pseudo R-wave during a normal interpulse period. By flipping the switch 98 to its opposite position a D-type flip-flop 134 is effectively inserted between the 10 KHz clock source and the clock input to the scanner chips 92 and 94. The flip-flop 134 effectively halves the clock rate and thereby slows down the scanning rate.

The current waveform on conductor 132 is then applied to the inverting input of an operational amplifier 136. The non-inverting input of this amplifier is connected to ground via a resistor 138 and a feedback resistor 140 is coupled between its output terminal 142 and the inverting input. As such, this arrangement effectively converts the current waveform in line 132 to a voltage waveform at junction 142. Attached to the non-inverting input of the operational amplifier 144 is the collector electrode of a NPN transistor 152 whose emitter electrode is connected to ground and whose base electrode is connected to circuits associated with the push button 7 or 8 in FIG. 1. Depending upon whether it is button 7 or 8 that is depressed, transistor 152 will be either conducting or non-conducting which results in either a positive going excursion or a negative-going excursion for the pseudo R-wave signal developed at the output junction 154.

The voltage appearing at the junction point 154 typically may be in the range of from 0 to 8 volts. If a signal of this magnitude were applied to the R-wave sensing amplifier of a pacemaker under test, it would necessarily result in damage to that circuitry. Thus, it is essential to scale down the voltage to a millivolt value which is compatible with the pacer under test. That is to say, the voltage at 154 is scaled down to the millivolt levels needed for the pacer interface and resistor 116 is used to "calibrate", or set-up the system such that the digital display value will correspond to the actual millivolt level being applied to the pacer. Typically, the analog output at 166 is 10 millivolts per 5.00 volts output at 154.

Again summarizing, the circuitry thus far described functions to selectively cause either a positive pseudo R-wave or a negative pseudo R-wave signal to appear at the output terminal 166 to which the pacer under test is to be connected. The amplitude of the pseudo R-wave signal is repetitively incremented on successive cycles and ultimately a level is reached at which further pacer pulses from the unit under test are inhibited. The shape or contour of the pseudo R-wave is governed by the data words stored in the ROM 126 and various wave shapes are selectable depending upon the setting of the select switch 99.

The three second timer 76 will not time out so long as the unit under test is still producing pacer pulses at appropriate time intervals. However, when the point is reached at which the pseudo R-waves are of a sufficient amplitude to effect resetting of that pulse generator, the timer 76 will not be reset and will ultimately time out, i.e., reach the end of the three second time interval. When this happens, the circuitry operates to present a visual display, in millivolts, of the amplitude of the pseudo R-wave which resulted in resetting of the pulse generator of the pacer under test. The manner in which the circuit operates to perform this function will now be described.

It can be seen that the output of the flip-flop 80, i.e., the output from NAND gate 84, is connected as a first input to a NOR gate 168 whose second input is applied thereto by way of the conductor 68. When these inputs are simultaneously low, a high signal will be applied to the cascaded one-shots 170 which function to emit gating pulses on its output lines 172, 174 and 176 at sequential time points $t_1$, $t_2$ and $t_3$. It is also to be noted that the pacer pulses emanating from the NOR gate 64 are applied by way of a conductor 178 to a first input of a NOR gate 180 whose outut is, in turn, coupled through an inverter 182 to the clock input terminal of the display counter 184. Because of the manner in which the inputs are applied to the counter 184, it is incremented upon the occurrence of each pacer pulse at terminal 60. The outputs from the individual stages of the display counter 184 are coupled through tri-state buffer circuits indicated generally by numeral 186 which are placed in an enabled condition by a control signal on the line 188. Again, either the closure of the +R-WAVE or the −R-WAVE push buttons 7 and 8 in FIG. 1 cause the necessary enable signal to appear on the conductor 188. Hence, so long as one or the other of these two push buttons is depressed, which is the situation when it is desired to obtain a sensitivity reading, at the conclusion of the time period (three seconds) established by the counter 76, the NOR gate 168 will output a signal to the cascaded one-shots 170 to cause the one-shots to, in turn, produce a $t_1$ pulse on conductor 172 and this pulse will be inverted by circuit 190 before being applied to the XFER input of the counter 184. When this happens, the contents of the counter are applied through the tri-state buffers 186 to the digit select decoder 192 and the bar select decoder 194. Depending upon the bit permutations of the signals applied to these last-mentioned devices, the particular 7-bar LED numeric display modules 196, 198, 200 and 202 will be selected for energization and the particular bar segments thereof will be illuminated. While the details of the interconnection of the selector outputs from circuits 192 and 194 to the display modules 196-202 are not illustrated in order to avoid needless confusion in the drawings, those interested in knowing how these interconnections should be made can gain this understanding by reference to the manufacturer's data sheets associated with the item in question.

Because the contents entered into the counter 184 correspond to the number of times that the amplitude select circuit 104 has been incremented and because each such incrementation leads to an increase in amplitude of the pseudo R-wave by a known amount, it can be seen that it is a simple matter to calibrate the counter 184 to display, in millivolts, the number of units of incrementation that had to take place to increase the pseudo R-wave amplitude to the point where the sensitivity circuit of the pacer under test would respond to it. A release and re-depression of the push button 7 or 8 will renew the cycle of operation and result in the presentation of a new display value following the requisite time periods needed to develop the output to be displayed.

Figure 3D:
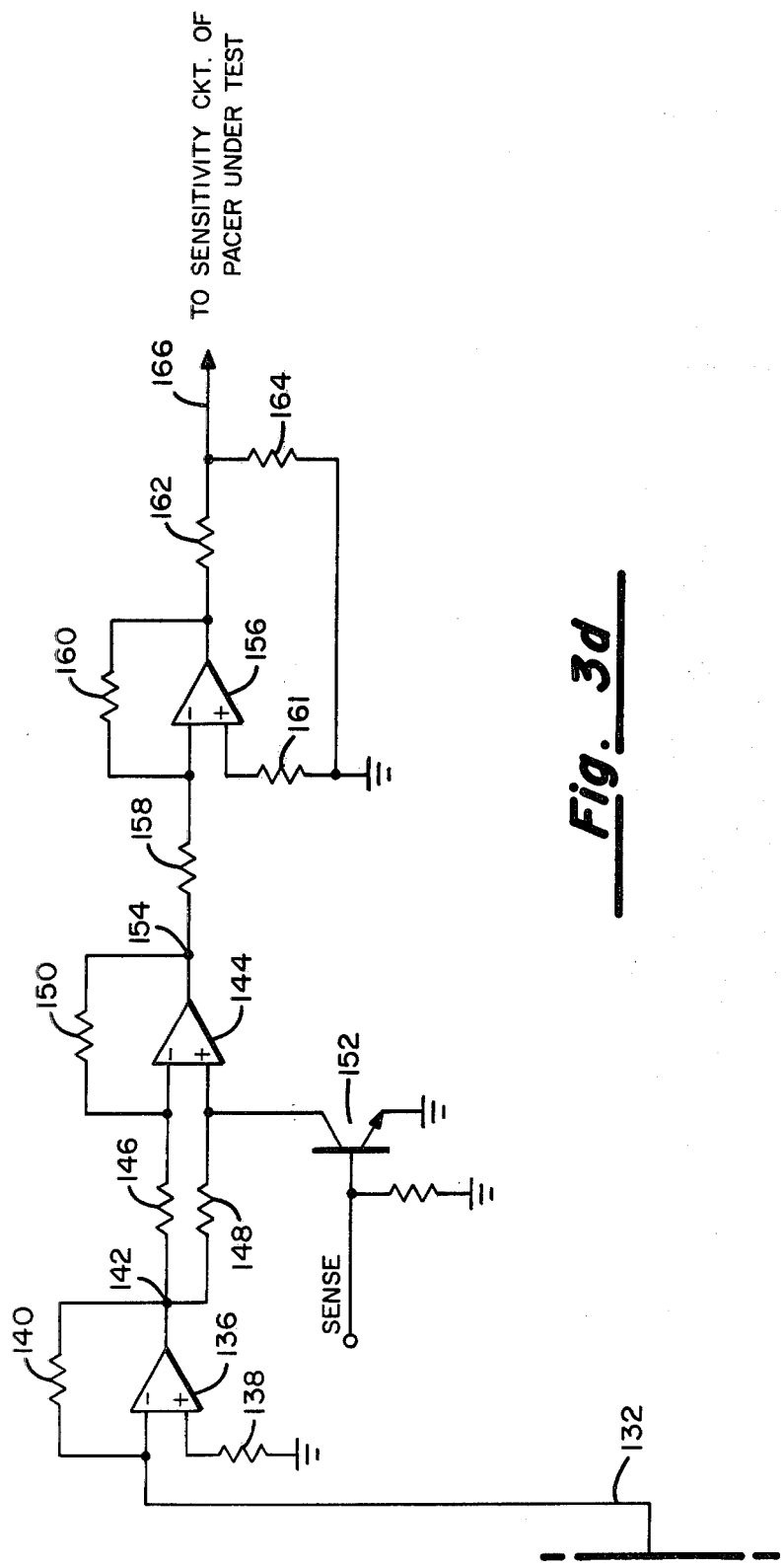
Figure 3B:
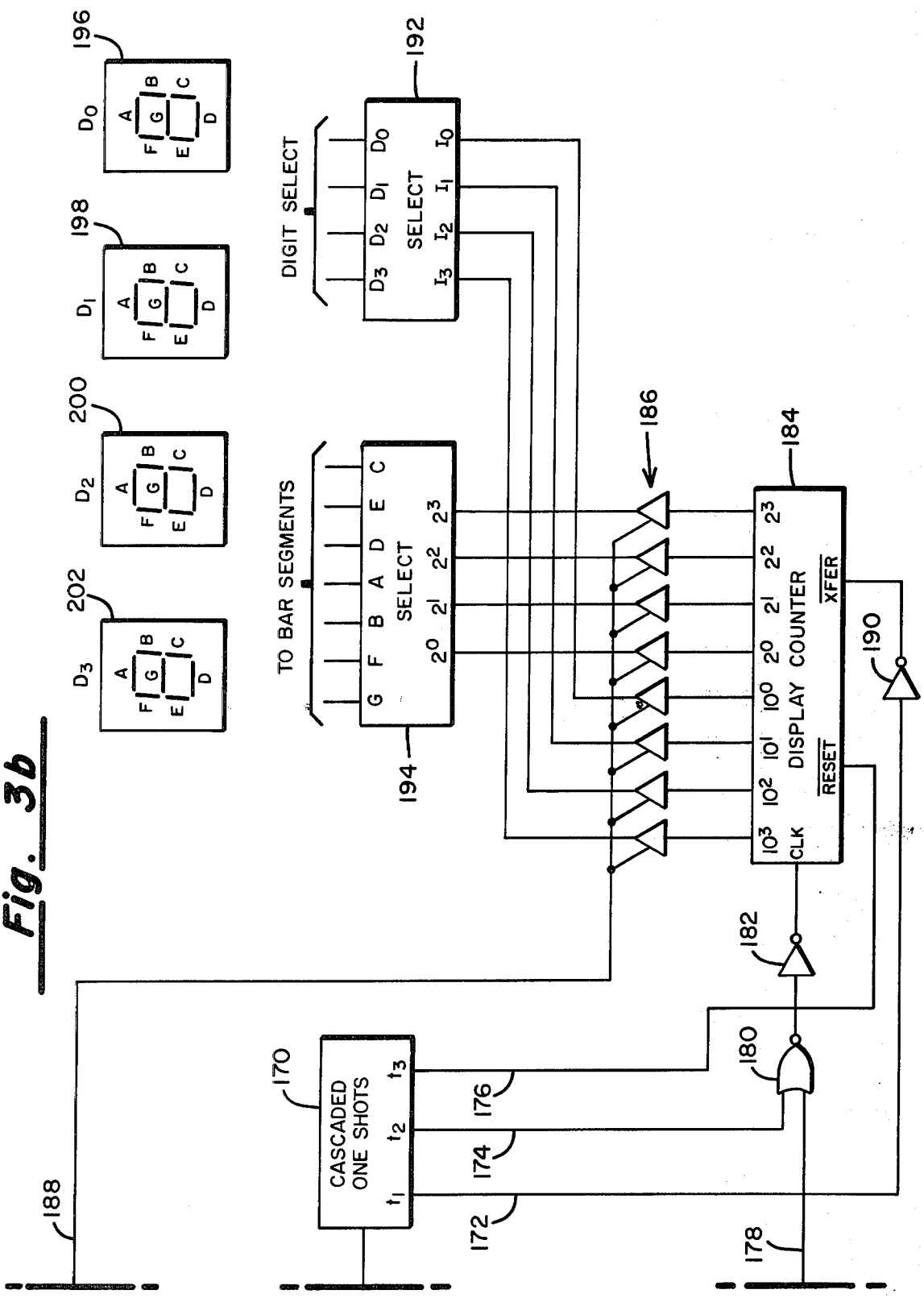
Figure 3C:
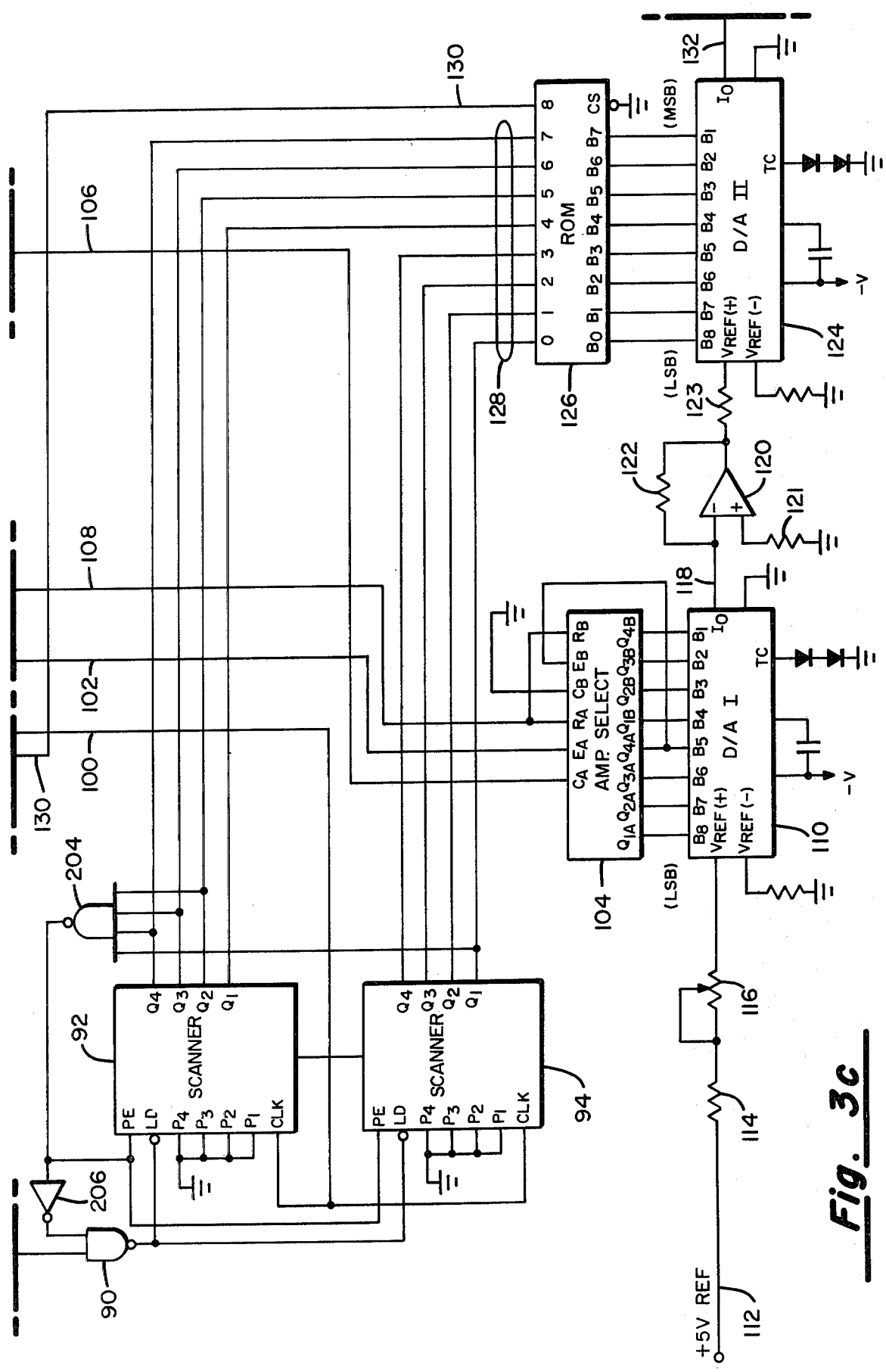

The NAND gate 204 associated with the scanner outputs provides a convenient means for shortcutting the scanner operation when fewer than the maximum number of addresses available in the ROM 126 are actually utilized. For example, when the NAND gate 204 has its inputs connected up as illustrated in FIG. 3c of the drawings, when a count of $225_{10}$ is reached, the gate 204 will be satisfied and a preload enable signal (P.E.) will be applied to the scanner inputs at the same time a signal will propagate through inverter 206 and NAND gate 90 to the load (LD) input terminals of the scanner chips 92 and 94 causing all zero's to be again jammed into the counter to re-initiate the generation of sequential addresses beginning at address zero. Were it not for the inclusion of the gate 204, the scanner would have to count to $511_{10}$ before again reaching its all zero condition.

Listed below are various component types and values which may be employed in implementing the invention. It is to be understood that these values are intended to be illustrative and not limitive, other values being operable also.

TABLE I

| ITEM | TYPE |
| --- | --- |
| 76 | 4040 B |
| 86 | 40102 B |
| 92, 94 | 14161 B |
| 104 | 4520 B |
| 110, 124 | DAC08 |
| 120, 136, 144, 156 | LM 124 |
| 126 | CDP 1832 |
| 184 | MK 5007 P |
| 192 | DS 75494 |
| 194 | 74 C 48 |
| 196–202 | MAN 3640 |
| $R_{114}$ | 2.32 K |
| $R_{116}$ | 500 |
| $R_{122,121}$ | 9.31 K |
| $R_{123}$ | 1.82 K |
| $R_{140,138}$ | 1.27 K |
| $R_{146,148,150,158,160}$ | 10 K |
| $R_{161}$ | 4.99 K |
| $R_{162}$ | 243 K |
| $R_{164}$ | 500 |

Thus it can be seen that there is provided by this invention a means whereby the threshold characteristic of an electronic circuit may be accurately measured and displayed. Those skilled in the art will recognize that various changes and modifications may be made to the embodiment described herein without departing from the spirit and scope of the invention. Accordingly, the scope of the invention is to be determined from the following claims.

What is claimed is:

1. Apparatus for measuring the R-wave sensitivity of a demand cardiac pacer comprising:
   (a) means for receiving pacer pulses from said cardiac pacer;
   (b) means responsive to successive ones of received pacer pulses for producing pseudo R-waves of incrementally increasing amplitude;
   (c) means for applying said pseudo R-wave signals to the R-wave sensing circuit of said cardiac pacer; and
   (d) means for displaying the voltage amplitude of the pseudo R-wave just sufficient to cause resetting of the pulse generator of said demand cardiac pacer.

2. Apparatus as in claim 1 wherein said means for receiving pacer pulses comprises:
   (a) a timer circuit adapted to be reset by the received pacer pulses;
   (b) a delay circuit triggered by each of said pacer pulses; and
   (c) counter means connected to receive said pacer pulses ad to be reset by the output produced by said timer means when a predetermined time measured by said timer means has elapsed.

3. Apparatus as in claim 2 wherein said means for generating pseudo R-waves comprises:
   (a) a first multiplying digital-to-analog converter connected to the output of said counter means;
   (b) scanner means coupled to said delay means for generating a plurality of digital address representing signals following the termination of the delay period of said delay means;
   (c) memory means having a plurality of digital words, each representing a signal amplitude at a given different discrete instant of time, said memory being connected to receive the digital address representing signals from said scanner means; and
   (d) a second multiplying digital-to-analog converter connected to receive the output from said first digital-to-analog converter and said digital words read out from said memory, the arrangement being such that the output from said second multiplying digital-to-analog converter constitutes an electrical signal whose contour is determined by said digital words and whose amplitude is determined by the instantaneous contents of said counter means.

4. Apparatus as in claim 3 and further including:
   (a) voltage scaling means coupled to the output of said second multiplying digital-to-analog converter for matching said output to the voltage range acceptable to said circuit under test.

5. Apparatus as in claim 1 wherein said display means comprises:
   (a) a second counter connected to be advanced by said pacer pulses;
   (b) a visual display device coupled to the output of said second counter means; and
   (c) means responsive to the output from said timer means for applying the digital value contained in said second counter means to said visual display device.

6. Apparatus for measuring the R-wave sensitivity response threshold of a demand cardiac pacer circuit comprising:
   (a) means for generating pseudo R-wave signals having an amplitude which is incremented in known, predetermined steps during successive cycles;
   (b) means for applying said generated pseudo R-wave signals to said pacer circuit;
   (c) means for sensing when said pacer circuit first responds to said generated pseudo R-wave signals; and
   (d) means for visually displaying the amplitude of the pseudo R-wave signal causing said pacer circuit to first respond to said generated pseudo R-wave signal.

* * * * *